(12) United States Patent
Pasha

(10) Patent No.: US 8,360,773 B2
(45) Date of Patent: Jan. 29, 2013

(54) DENTAL HIGH VOLUME SUCTION TUBE WITH PROTECTIVE CAP

(76) Inventor: Faheem Pasha, Albuquerque, NM (US)

( * ) Notice: Subject to any disclaimer, the term of this patent is extended or adjusted under 35 U.S.C. 154(b) by 24 days.

(21) Appl. No.: 13/066,573

(22) Filed: Apr. 18, 2011

(65) Prior Publication Data

US 2012/0264080 A1    Oct. 18, 2012

(51) Int. Cl.
*A61C 17/06*    (2006.01)
(52) U.S. Cl. .......................................... 433/96; 604/902
(58) Field of Classification Search .................... 433/91, 433/96; 604/902
See application file for complete search history.

(56) References Cited

U.S. PATENT DOCUMENTS

| | | | | |
|---|---|---|---|---|
| 950,109 | A * | 2/1910 | Levkowicz | 433/91 |
| 1,184,922 | A * | 5/1916 | Brownton | 433/91 |
| 2,130,406 | A * | 9/1938 | Angell | 433/91 |
| 2,742,701 | A * | 4/1956 | Berger | 433/96 |
| 3,256,885 | A * | 6/1966 | Higgins et al. | 604/268 |
| 3,373,492 | A * | 3/1968 | Batch | 433/91 |
| 4,490,138 | A * | 12/1984 | Lipsky et al. | 604/40 |
| 5,015,184 | A * | 5/1991 | Perry et al. | 433/93 |
| 5,066,228 | A * | 11/1991 | Doundoulakis et al. | 433/91 |
| 5,181,907 | A * | 1/1993 | Becker | 604/22 |
| 5,380,245 | A * | 1/1995 | Reiterman et al. | 454/63 |
| 5,690,487 | A * | 11/1997 | Whitehouse et al. | 433/91 |

* cited by examiner

*Primary Examiner* — Ralph Lewis
(74) *Attorney, Agent, or Firm* — The Adams Law Firm

(57) ABSTRACT

This invention is a hollow, crown shaped cap along with the dental High Volume Evacuation (HVE) tube into which the cap is specially designed to fit. The crown shaped cap is detachable and attachable. The invention may also be produced as one piece, with the cap permanently attached. The crown shaped cap extends outward from the suction end, and is larger in diameter than the HVE tube. This crown shaped cap for the HVE dental suction tube consists of four tubular, question mark-shaped parts which intersect to form four openings for suction. The cap is hollow and has a short tubular end. The cap is attached to the suction end of the HVE tube by snapping the tubular end of the cap into the suction end of the HVE tube.

The crown shaped cap facilitates retraction of the tongue, cheeks or lips within, and about, the oral cavity. It also enables a dentist to work on teeth without the danger of causing tissue plug injury to the retracted tongue, cheek or lips, while still allowing suction of larger particles. The invention is designed to be disposable, for single use.

1 Claim, 1 Drawing Sheet

DENTAL HIGH VOLUME SUCTION TUBE WITH PROTECTIVE CAP

BACKGROUND OF THE INVENTION

The present invention is a cap and a tube for high volume dental suction. One end of the tube is designed to fit the cap.

High volume evacuation (HVE) suctions are used during dental procedures to remove saliva and particles, such as plaque, calculus, parts of existing fillings and decayed tooth material. Such HVE suction includes a suction tube having a distal (upper) suction end and a proximal (lower) discharge end. The discharge end of the suction tube is connected via a hose and hose valve to a vacuum source. The distal (upper) end of the suction tube is inserted into a patient's mouth.

The HVE suction tube is typically made of polyvinyl chloride or polyethylene. Such tips are hard and the edges rather sharp, which can irritate the tissue of a patient's mouth.

The suction draws material into the opening and down the tube. If the tip contacts the patient's mouth tissue, it can suck the tissue into the tip, obstructing the suction. This is uncomfortable and can cause damage to the patient's mouth and make it more difficult for the dental user. Such HVE suction tubes can require constant manual adjustments to maintain efficient suction while in use and cause unpleasant sensations, bruising and anxiety to patients

SUMMARY OF INVENTION

It is an objective of the present invention to provide a protective suction cap, and the specially designed HVE tube onto which it fits; the invention overcomes the aforementioned difficulties with existing HVE suction tube.

The HVE tube of the invention includes a tube having a suction end and a discharge end and which can be used with or without the protective cap attached.

The invention can also be produced as one piece, with the cap permanently attached to the HVE tube.

The cap provides a gap between suction end of the HVE tube and the oral tissue, to simultaneously allow tissue retraction and suction in the working area of an oral cavity, without causing trauma to fragile tissue.

The invention is made of polyethylene or other suitable plastic.

DETAILED DESCRIPTION OF THE INVENTION

Figure 1:
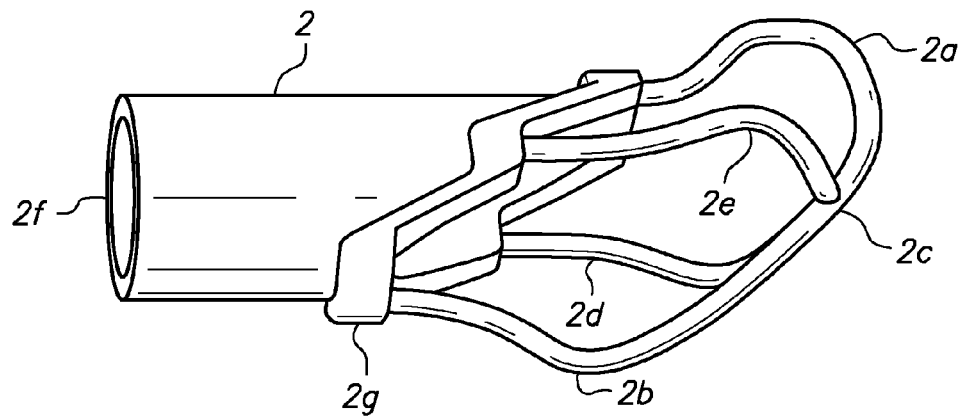
FIG. 1 is a right side view of the crown shaped cap.
Figure 2:
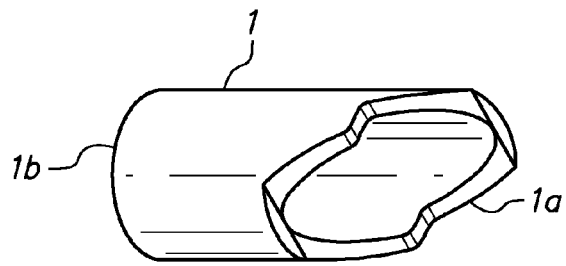
FIG. 2 is a right side view of the HVE suction tube of the present invention, specially designed to fit onto the crown shaped cap by pressing the cap into the suction end of the HVE tube.
Figure 3:
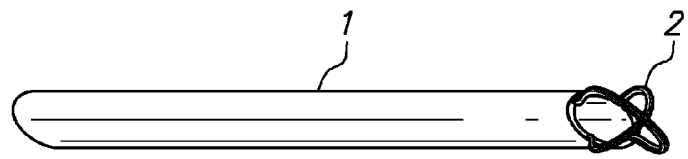
FIG. 3 is a side view of the HVE suction tube with crown shaped tip permanently attached on the suction end as one piece.

The present invention in the embodiments shown in the drawings includes an HVE suction tube 1 having a suction or distal end 1a, and a discharge or proximal end 1b, the end 1b attached to flexible tubing that attaches to the source of suction. The distal end of the tube has a crown-shaped, cage-like cap or structure. The cap-like structure may be detachably connected to tube 1 at the distal end 1a as shown best in FIG. 1. Alternatively, in the embodiment shown best in FIGS. 3 and 3A, the cage-like structure may be integral with the tube 1, the tube and cap-like structure molded of plastic material such as polyvinyl fluoride or polyethylene, materials well known in the field of dentistry. The tube 1 typically has a length of 4-6 inches and an internal diameter of approximately ¼ inch with a wall thickness of approximately 1/32 inch. The distal end of tube 1, as seen best in FIGS. 1 and 2, is severed to form an edge in a plane that is acute to the longitudinal axis of the tube 1. As shown in FIG. 2, the edge may have steps with corresponding and complementary steps formed in the short attachment section 2g of the cage-like structure 2 to provide a secure support for the cap 2 on tube 1.

The cage-like structure or cap 2 as noted above has a short tubular section indicated at 2g fitted over the end of tube 1 in frictional engagement therewith. The cage-like structure 2 comprises in the embodiment shown four vanes or struts indicated at 2a, 2h, 2d, and 2e, although three vanes or struts may be employed depending on the plastic material chosen for forming the cap.

Figure 3A:
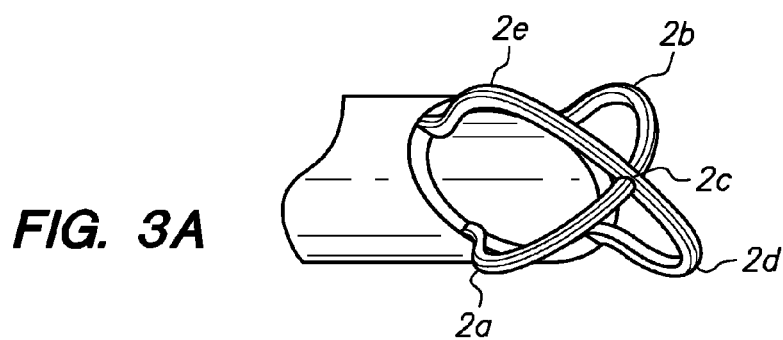
FIG. 3A is a closer cutaway view of FIG. 2. It is a portion of the HVE tube with the crown shape cap permanently attached directly to the suction end of the HVE tube.

Each of the vanes or struts 2a, 2b, 2d, 2e has a question-mark shape which include a short straight or slightly curved proximal section and a curved convex distal section. The proximal end of the proximal sections are attached to and may be integral with the ring portion 2g of the cap-like structure that attaches to the distal end of tube 1 as shown in FIG. 1 or at the tube edge as seen best in FIG. 3A. At the distal end of each distal section of the vanes or struts the ends are attached to the corresponding end of each of the other vanes or struts at 2c. It will be understood that each of the vanes may be molded in plastic as an integral structure. Each of the vanes may have a circular cross section as shown in FIG. 1 or a polygonal cross section as shown in FIG. 3A.

The vanes or struts of the cage-like structure or cap 2 have a diameter, as measured on a plane that is transverse to the axis of the tube that is greater than the inner diameter and/or outer diameter of the tube 1. The cap-like structure or cap 2 extends axially or longitudinally from the distal end of the tube 1a distance greater than the inner or outer diameter of tube 1.

It will therefore be seen that the area as measured between each pair of vanes or struts, in the aggregate, is greater than the cross-sectional area of tube 1. It will also be appreciated that the cage-like structure is slightly resilient such that when inserted into the patient's mouth, it may distort slightly but will prevent the oral tissue from blocking the distal open end of tube 1 or from being aggravated. The area is thus large enough for suction uptake of larger particles that may be generated during dental processes.

In operation, the distal end of the tube 1 with the cage-like cap 2 is inserted into the patient's mouth such that the cap is in contact with the patient's oral tissue. When suction is applied, the cap 2 will prevent or minimize any plugging of the end of the suction tube by tissue while still allowing suction to remove the unwanted materials from the oral cavity. The cap 2 thus eliminates the danger of the tissue being grabbed or forcibly pressed against the end of the tube which is frequent with existing dental suction tubes commonly used in dental practices today.

It will be obvious to those having skill in the art that many changes may be made to the details of the above-described invention without departing from the underlying principles thereof. The scope of the present invention should, therefore be determined only by the following claims.

The invention claimed is:
1. A dental suction tube for evacuating saliva and debris from a patient's mouth comprising, an elongated tubular member having a longitudinal central axis and including a distal end; and
 a cage structure at the tubular member distal end comprising four spaced apart vanes, each vane having a question-mark shape with a generally straight proximal section that extends from the tubular member distal end, a mid-section that curves outwardly away from the longitudinal central axis and a curved distal section that curves back to the longitudinal central axis, the straight section proximal end supported on the end of the tube and the distal ends of the curved distal sections of each vane attached to one another.

* * * * *